US00PP24243P2

(12) United States Plant Patent
Takahashi

(10) Patent No.: US PP24,243 P2
(45) Date of Patent: Feb. 11, 2014

(54) ***GENTIANA* PLANT NAMED 'HAKURYU'**

(50) Latin Name: *Gentiana hybrida*
Varietal Denomination: Hakuryu

(75) Inventor: Shunichi Takahashi, Hanamaki (JP)

(73) Assignee: T & G Bionursery Co., Ltd., Hanamaki-shi, Iwate-perfecture (JP)

( * ) Notice: Subject to any disclaimer, the term of this patent is extended or adjusted under 35 U.S.C. 154(b) by 133 days.

(21) Appl. No.: 13/385,290

(22) Filed: Feb. 10, 2012

(51) Int. Cl.
*A01H 5/00* (2006.01)

(52) U.S. Cl.
USPC ..... Plt./433

(58) Field of Classification Search
USPC ..... Plt./433
See application file for complete search history.

*Primary Examiner* — June Hwu
(74) *Attorney, Agent, or Firm* — C. A. Whealy

(57) ABSTRACT

A new and distinct cultivar of *Gentiana* plant named 'Hakuryu', characterized by its upright plant habit; moderately vigorous growth habit; moderately strong flowering stems; relatively short leaves; freely branching habit; freely flowering habit; and large white-colored flowers.

2 Drawing Sheets

Botanical designation: *Gentiana hybrida.*
Cultivar denomination: 'HAKURYU'.

BACKGROUND OF THE INVENTION

The present invention relates to a new and distinct cultivar of *Gentiana* plant, botanically known as *Gentiana hybrida*, typically grown as a cut flower, and hereinafter referred to by the name 'Hakuryu'.

The new *Gentiana* plant is a product of a planned breeding program conducted by the Inventor in Hanamki-shi, Iwate-prefecture, Japan. The objective of the breeding program is to create new *Gentiana* plants with large and attractive flowers.

The new *Gentiana* plant originated from a cross-pollination made by the Inventor in October, 2002, of a proprietary selection of *Gentiana hybrida* identified as code name GW, not patented, as the female, or seed, parent with *Gentiana hybrida* 'Sawada Shiro', not patented, as the male, or pollen, parent. The new *Gentiana* plant was discovered and selected by the Inventor as a single flowering plant from within the progeny of the stated cross-pollination grown in a controlled greenhouse environment in Hanamki-shi, Iwate-prefecture, Japan in October, 2005.

Asexual reproduction of the new *Gentiana* plant by tissue culture in Hanamki-shi, Iwate-prefecture, Japan, since April, 2006, has shown that the unique features of this new *Gentiana* plant are stable and reproduced true to type in successive generations.

SUMMARY OF THE INVENTION

Plants of the new *Gentiana* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Hakuryu'. These characteristics in combination distinguish 'Hakuryu' as a new and distinct *Gentiana* plant:

1. Upright plant habit.
2. Moderately vigorous growth habit.

3. Moderately strong flowering stems.
4. Relatively short leaves.
5. Freely branching habit.
6. Freely flowering habit.
7. Large white-colored flowers.

Plants of the new *Gentiana* differ primarily from plants of the female parent selection in the following characteristics:

1. Plants of the new *Gentiana* are taller than plants of the female parent selection.
2. Plants of the new *Gentiana* are more freely branching than plants of the female parent selection.
3. Plants of the new *Gentiana* and the female parent selection differ in leaf shape.
4. Plants of the new *Gentiana* flower earlier than plants of the female parent selection.

Plants of the new *Gentiana* differ primarily from plants of the male parent, 'Sawada Shiro', in the following characteristics:

1. Plants of the new *Gentiana* are shorter than plants of 'Sawada Shiro'.
2. Plants of the new *Gentiana* are more freely branching than plants of 'Sawada Shiro'.
3. Plants of the new *Gentiana* and 'Sawada Shiro' differ in leaf shape.
4. Plants of the new *Gentiana* flower later than plants of 'Sawada Shiro'.

Plants of the new *Gentiana* can be compared to plants of the *Gentiana* 'Shinsetsu', not patented. In side-by-side comparisons conducted in Hanamki-shi, Iwate-prefecture, Japan, plants of the new *Gentiana* differed from plants of 'Shinsetsu' in the following characteristics:

1. Plants of the new *Gentiana* had longer flowering stems and longer internodes than plants of 'Shinsetsu'.
2. Plants of the new *Gentiana* were more freely branching than plants of 'Shinsetsu'.
3. Plants of the new *Gentiana* had smaller leaves than plants of 'Shinsetsu'.
4. Plants of the new *Gentiana* flowered later than plants of 'Shinsetsu'.

5. Plants of the new *Gentiana* and 'Shinsetsu' differed in flower color as plants of 'Shinsetsu' had light yellow green-colored flowers.

BRIEF DESCRIPTION OF THE PHOTOGRAPHS

The accompanying colored photographs illustrate the overall appearance of the new *Gentiana* plant showing the colors as true as it is reasonably possible to obtain in colored reproductions of this type. Colors in the photographs may differ slightly from the color values cited in the detailed botanical description which accurately describe the actual colors of the new *Gentiana* plant.

The photograph on the first sheet comprises a side perspective view of typical flowering stems of 'Hakuryu'.

The photograph on the second sheet is a close-up view of a typical flower of 'Hakuryu'.

DETAILED BOTANICAL DESCRIPTION

Plants used for the aforementioned photographs and following description were grown under environmental conditions and cultural practices which closely approximate commercial production conditions during the summer in an outdoor nursery in Hanamki-shi, Iwate-prefecture, Japan. During the production of the plants, summer day temperatures averaged 26.4° C. and night temperatures averaged 23.6° C. Plants were three years old when the photographs and description were taken. In the following description, color references are made to The Royal Horticultural Society Colour Chart, 2001 Edition, except where general terms of ordinary dictionary significance are used.

Botanical classification: *Gentiana hybrida* 'Hakuryu'.

Parentage:

*Female parent.*—Proprietary selection of *Gentiana hybrida* identified as code name GW, not patented.

*Male parent.*—*Gentiana hybrida* 'Sawada Shiro', not patented.

Propagation:

*Type.*—By tissue culture.

*Time to initiate roots.*—About two to three weeks at soil temperatures of 15° C. to 25° C.

*Time to produce a rooted young plant, winter.*—About two months at soil temperatures ranging from 15° C. to 20° C.

*Root description.*—Fine, fibrous; white in color.

*Rooting habit.*—Moderate branching; medium density.

Plant description:

*Plant and growth habit.*—Perennial cut flower plant; upright plant habit; moderately strong flowering stems; freely branching habit; about ten flowering stems develop per plant; moderately vigorous growth habit; campanulate flowers arranged in terminal and axillary clusters.

*Plant height.*—About 80 cm.

*Flowering stem description.*—Length: About 34.5 cm. Diameter: About 2 mm. Internode length: About 4.9 cm. Texture: Smooth, glabrous. Color: Close to 147C.

Foliage description:

*Arrangement.*—Opposite, simple; sessile.

*Length.*—About 4.5 cm.

*Width.*—About 2 cm.

*Shape.*—Ovate.

*Apex.*—Acute.

*Base.*—Attenuate.

*Margin.*—Entire.

*Texture, upper and lower surfaces.*—Smooth, glabrous.

*Venation pattern.*—Pinnate, reticulate.

*Color.*—Developing leaves, upper surface: Close to 143B. Developing leaves, lower surface: Close to 143C. Fully expanded leaves, upper surface: Close to 143A; venation, close to 139D. Fully expanded leaves, lower surface: Close to 143C; venation, close to 139C.

Flower description:

*Flower arrangement, shape and habit.*—Campanulate flowers arranged in terminal and axillary clusters; flowers face mostly upright; freely flowering habit, about 42 flowers develop per inflorescence.

*Natural flowering season.*—Plants begin flowering mid October in Hanamki-shi, Iwate-prefecture, Japan; flowers open when temperatures are above 20° C. and close when temperatures are below 20° C.

*Flower longevity as a cut flower.*—About two weeks; flowers persistent.

*Fragrance.*—None detected.

*Flower buds.*—Length: About 1.1 cm. Diameter: About 5 mm. Shape: Deltoid. Color: Close to 138D.

*Flower diameter.*—About 1.6 cm.

*Flower depth (height).*—About 3.9 cm.

*Petals.*—Arrangement: About five in a single whorl; fused. Length: About 1 cm. Width: About 1 cm. Shape: Ovate. Apex: Acute. Margin: Entire. Texture, upper and lower surfaces: Smooth, glabrous. Color: When opening and fully opened, upper surface: Close to 155B; spots, close to 144A. When opening and fully opened, lower surface: Close to 155B.

*Sepals.*—Arrangement: About five in a single whorl; fused. Length: About 1.9 cm. Width: About 3.9 mm. Shape: Narrowly lanceolate. Apex: Acute. Margin: Entire. Texture, upper and lower surfaces: Smooth, glabrous. Color, upper and lower surfaces: Close to 138D.

*Reproductive organs.*—Stamens: Quantity per flower: Five. Anther shape: Spatulate. Anther length: About 4 mm. Anther color: Close to 153D. Pollen amount: Moderate. Pollen color: Close to 153D. Pistils: Quantity per flower: One. Pistil length: About 3.2 cm. Stigma shape: Two-parted. Stigma color: Close to 150D. Style length: About 2 cm. Style color: Close to 150D. Ovary color: Close to 150D.

*Seeds and fruits.*—Seed and fruit production have not been observed on plants of the new *Gentiana*.

Disease/pest resistance: Plants of the new *Gentiana* have not been noted to be resistant to pathogens and pests common to *Gentiana*.

Garden performance: Plants of the new *Gentiana* have exhibited good tolerance to rain, wind and temperatures ranging from about −13° C. to about 34° C.

It is claimed:

1. A new and distinct *Gentiana* plant named 'Hakuryu' as illustrated and described.

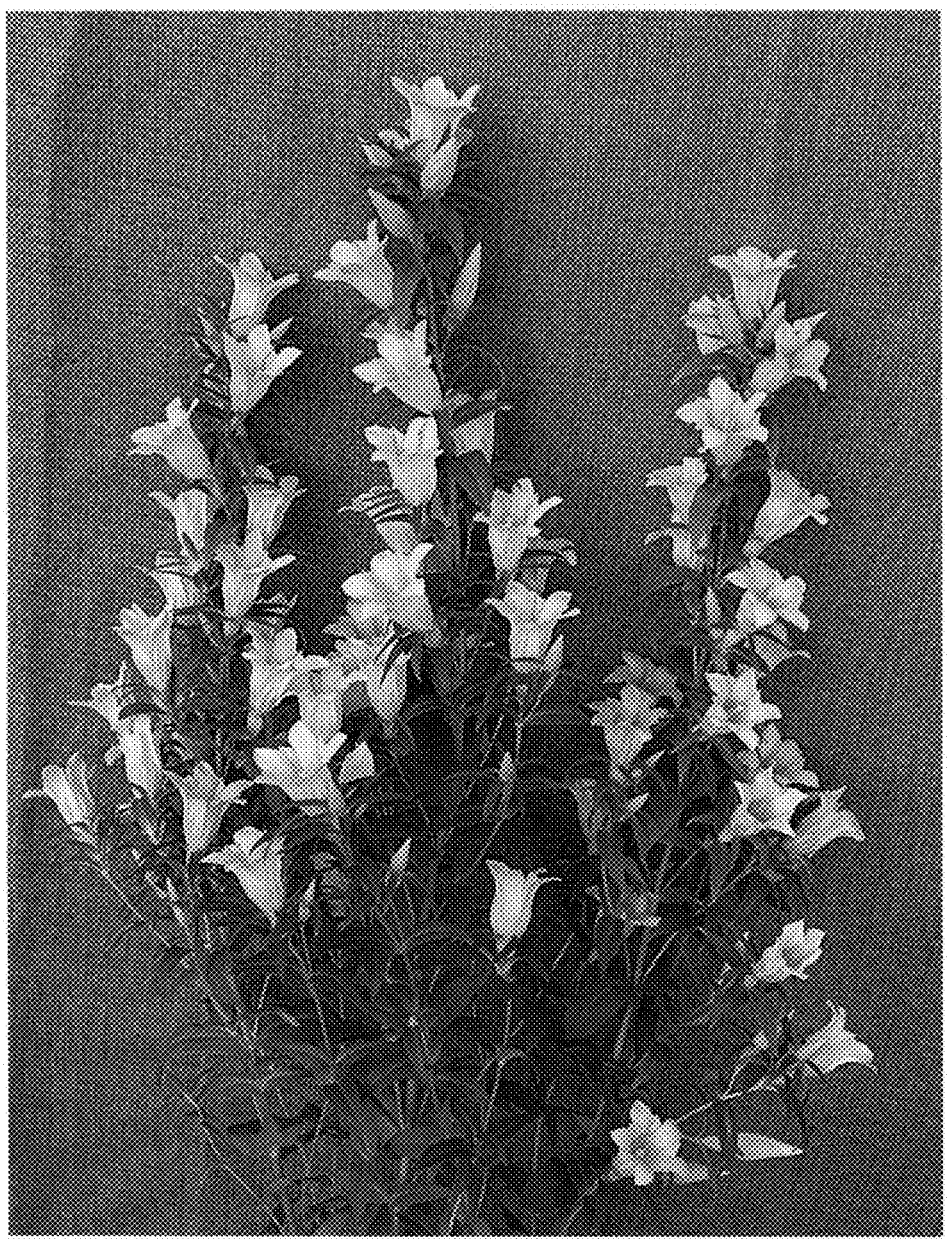

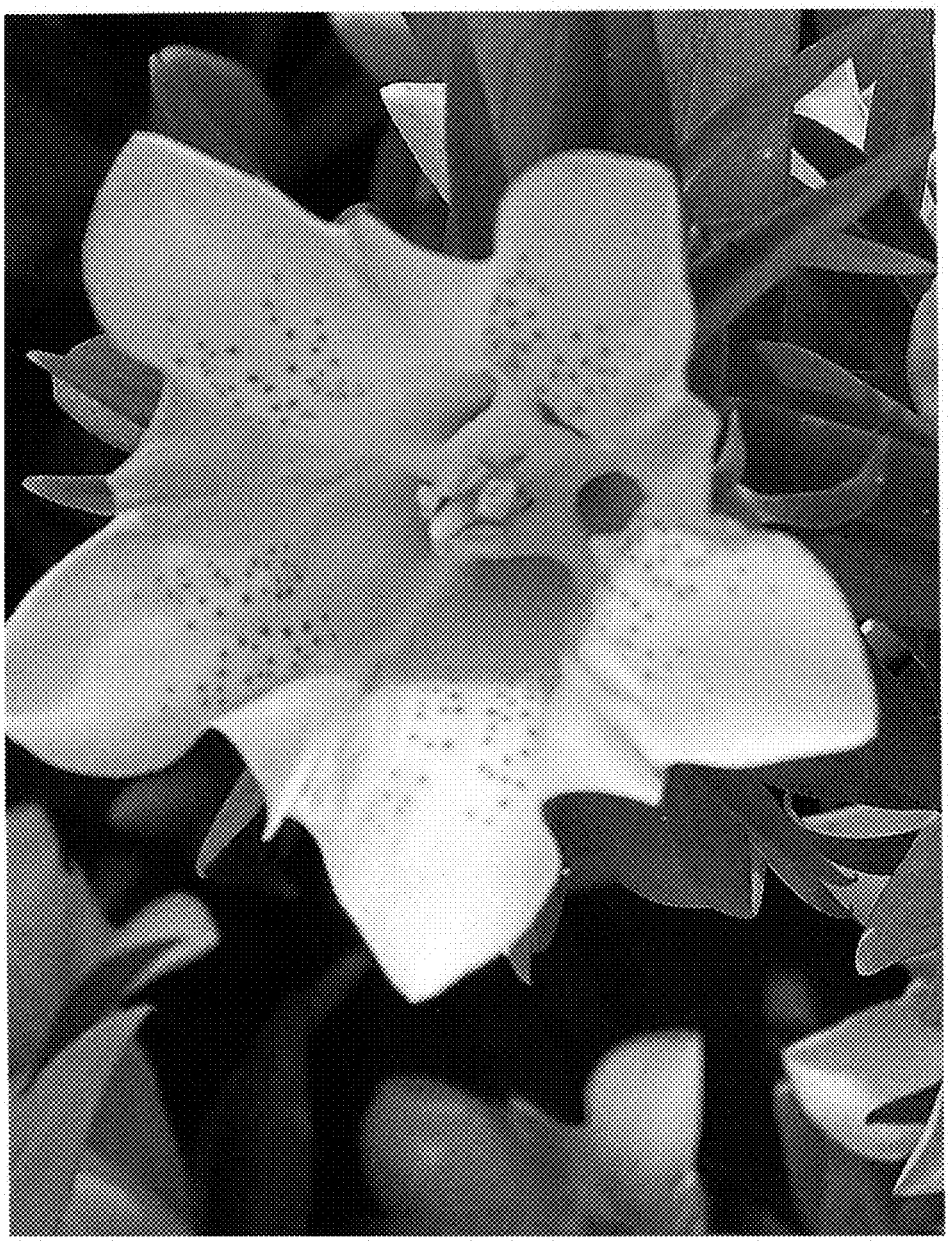

* * * * *